United States Patent [19]

March

[11] Patent Number: 5,070,867
[45] Date of Patent: Dec. 10, 1991

[54] FOOT THERAPY APPARATUS AND METHOD

[76] Inventor: John P. March, 3759 Erlewine Cir., Sacramento, Calif. 95819

[21] Appl. No.: 518,487

[22] Filed: May 3, 1990

[51] Int. Cl.[5] .......................... A61F 5/00; A61F 5/14; A43B 7/32
[52] U.S. Cl. ................................. 128/80 D; 128/586; 128/582; 128/581; 128/83.5; 36/91; 36/136
[58] Field of Search ..................... 128/80 D, 581, 586, 128/607, 610, 613, 83.5; 36/91, 110, 132, 136; 2/239

[56] References Cited

U.S. PATENT DOCUMENTS

| | | | |
|---|---|---|---|
| 1,702,661 | 2/1929 | Moran | 2/239 |
| 2,634,723 | 4/1953 | Wright . | |
| 3,086,520 | 4/1963 | Scholl . | |
| 3,566,487 | 3/1971 | Beightol | 36/110 |
| 4,774,776 | 10/1988 | Gulli . | |
| 4,821,432 | 4/1989 | Reiber | 128/83.5 X |

FOREIGN PATENT DOCUMENTS 2073260 12/1969 France .

Primary Examiner—Richard J. Apley
Assistant Examiner—Linda C. M. Dvorak
Attorney, Agent, or Firm—Thomas R. Lampe

[57] ABSTRACT

An orthopedic support including a layer of cushioning material is attached to the bottom surface of the arch portion of an article of footwear so that virtually all of the support for a wearer's foot is provided by the arch portion.

6 Claims, 3 Drawing Sheets

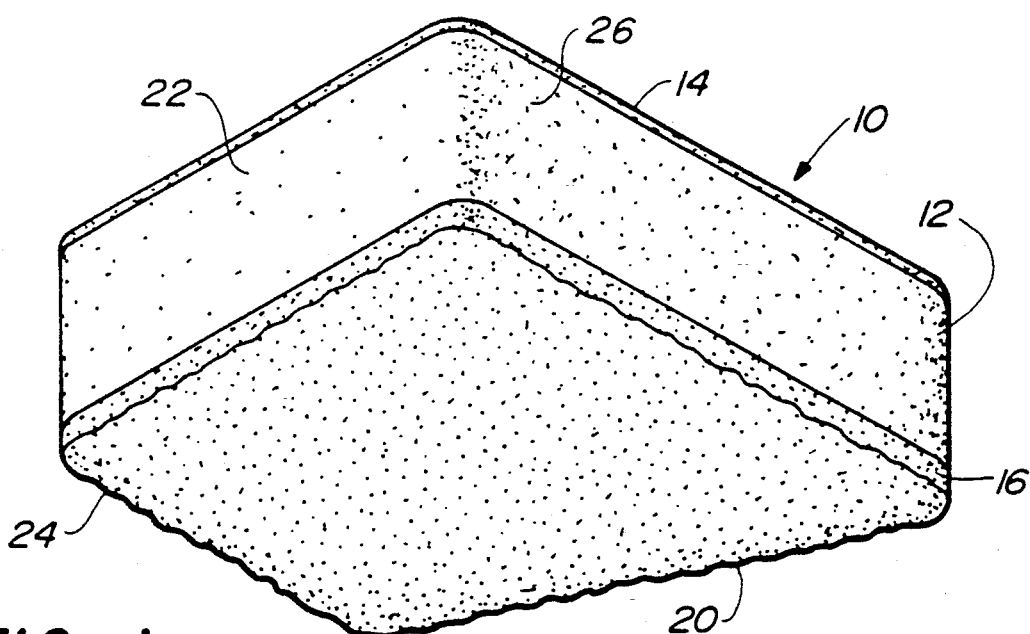
FIG._1
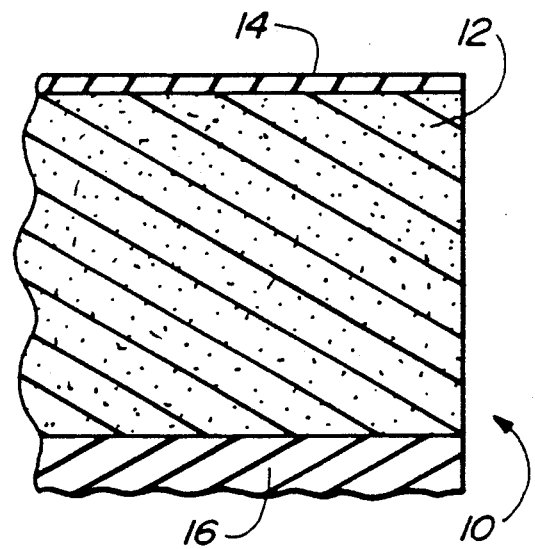
FIG._3A
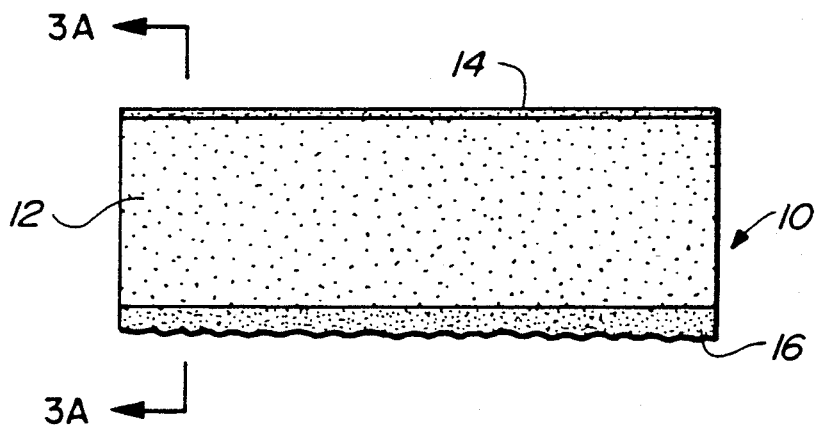
FIG._3

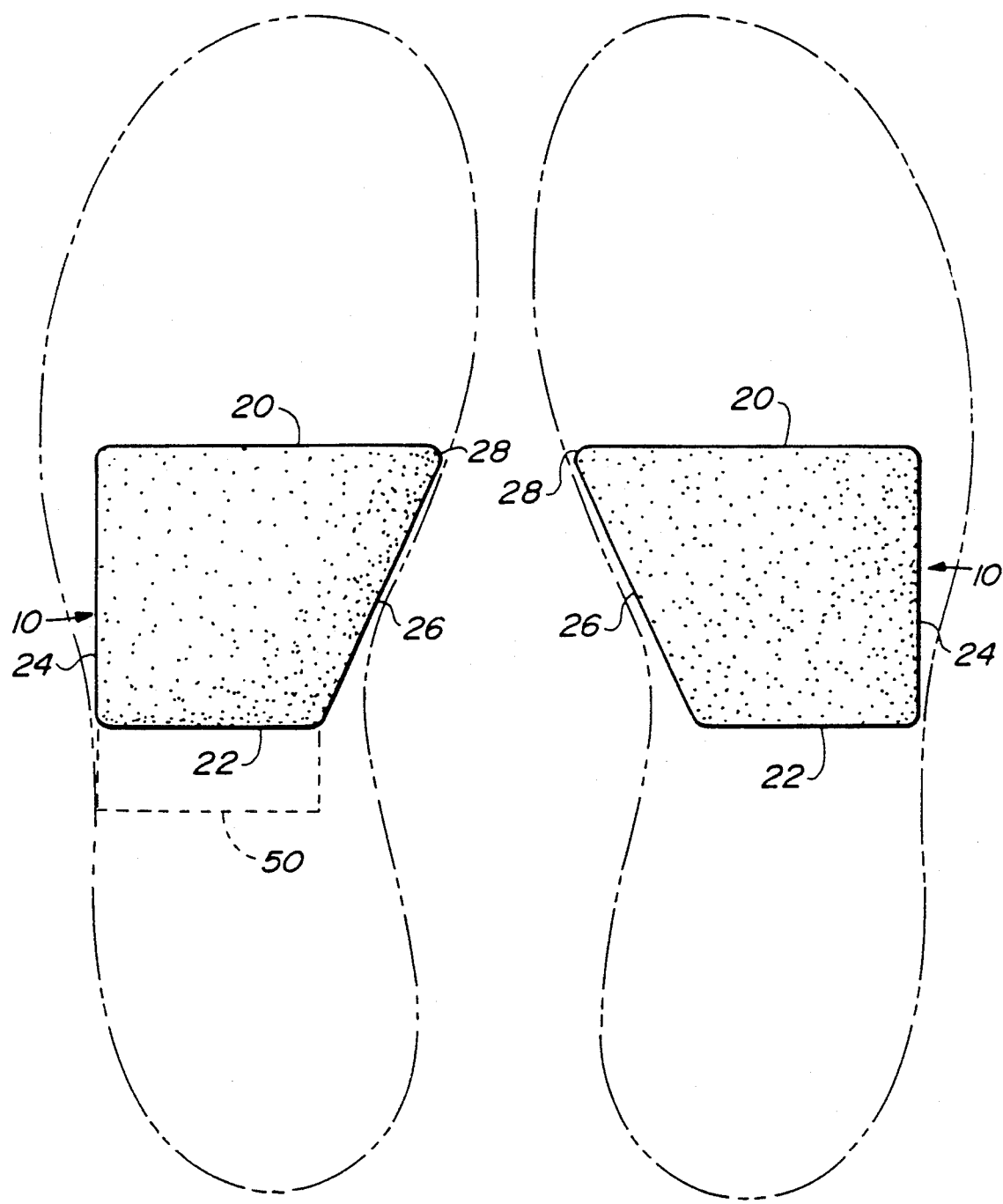
FIG._2A    FIG._2B

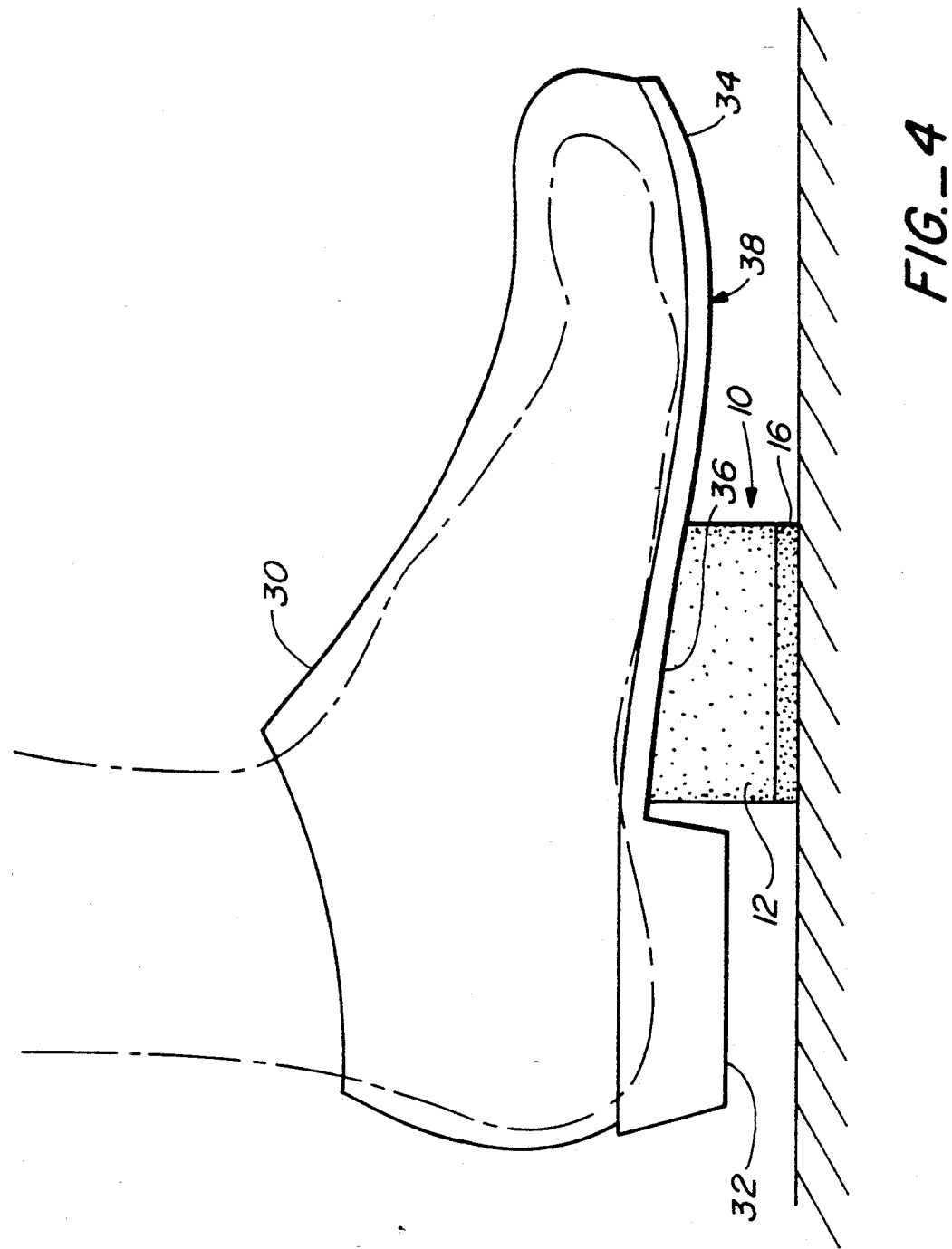
FIG._4

FOOT THERAPY APPARATUS AND METHOD

TECHNICAL FIELD

This invention relates to orthopedic apparatus, and more particularly to apparatus which both protects and massages a foot during conventional walking activity to promote and stimulate the circulation of blood within the foot for therapeutic purposes. The apparatus can be employed to promote healing in a foot which has been damaged or diseased. For example, the present invention may be employed by diabetics in the treatment of foot ulcers.

BACKGROUND ART

There are millions of diabetics within the United States and almost 20% of all people with diabetes who enter a hospital are admitted for foot problems. One of the most common of these problems is the foot ulcer. Neglecting these ulcers can result in infections, which in turn can lead to gangrene and amputation. The physician treating a diabetic with such problems will frequently prescribe hospitalization and require that the patient stay completely off his or her feet for an extended period of time.

When a patient is considered to be ambulatory, a total foot cast will often be applied to the diseased foot. This method is quite costly and, needless to say, is also extremely inconvenient. In conjunction with a cast, or sometimes as an alternative thereto, the patient may be required to utilize crutches to maintain the ulcerated or otherwise damaged portions of the foot out of contact with the ground. Impact of the damaged portion of the foot often aggravates the problem.

Because of the inconvenience and expense of these methods, patients sometimes choose not to follow such treatment, with tragic consequences such as amputation of all or part of the foot. Furthermore, these prior art approaches do nothing to stimulate the circulation of blood flow within the foot which has been shown to greatly encourage healing.

By way of contrast, the apparatus of the present invention is inexpensive and convenient to utilize. The apparatus enables the patient to walk in a normal fashion and by this very act stimulate blood circulation within the foot to speed up the healing process. The apparatus also serves to prevent damage to or significant impact upon the heel, ball of the foot, or on the bottom of the big toe, areas of the foot which are most likely to develop foot ulcerations.

As will be seen in greater detail below, the apparatus of the invention includes footwear such as a conventional shoe in combination with a particular type of orthopedic support. While patents do exist which disclose walking heels, supports and other attachments for casts and shoes, they are not appropriate for the therapeutic treatment of a wearer's foot. Even more particularly, there is no teaching in the prior art of the structural combination of the present invention which functions to protect the heel and toe area during walking while simultaneously promoting the circulation of blood within the foot to encourage the healing process.

U.S. Pat. No. 2,634,723 relates to a walking heel of resilient rubber construction used by patients having a foot or leg in a plaster cast.

U.S. Pat. No. 3,086,520 discloses a metatarsal support which is attached to a foot by an encircling band and used to provide firm support for a dropped metatarsal arch.

U.S. Pat. No. 4,774,776 is a bouncing attachment applied to a shoe which provides a bounce for the user when walking, running and jumping.

French Pat. No. 2,073,260 relates to an attachment for a hiking boot or the like to provide improved traction.

DISCLOSURE OF INVENTION

The present invention relates to a structural combination which suspends the ball and heel area of the wearer's foot up off the ground by supporting the foot under the arch. The apparatus includes footwear and an orthopedic support of a prescribed character attached to the footwear at a specific location thereon. The footwear and orthopedic support cooperate in such a manner that very little pressure is exerted on either the ball, toe, or heel area of the foot, even during the activity of walking. Furthermore, it has been found that the present arrangement actually promotes healing of sores on the toe, ball or heel areas of a foot, not only by keeping these areas substantially pressure-free but also by encouraging the circulation of blood. This latter action is accomplished by applying a gentle massaging action to the bottom of the foot during walking.

The footwear employed when carrying out the teachings of the invention has a heel portion, a toe portion and an arch portion between the heel portion and toe portion. The footwear has a bottom surface defined by said portions.

An orthopedic support including a layer of cushioning material is attached to the footwear bottom surface at the arch portion. The orthopedic support has a front end, a rear end, and opposed sides extending between the front and rear ends and generally conforming in shape to opposed sides of the arch portion. The orthopedic support is substantially confined to the area of the arch portion whereby virtually all of the support for a wearer's foot is provided by the arch portion when the wearer steps on the footwear with the orthopedic support positioned on a support surface.

The orthopedic support further includes a layer of adhesive and a layer of strong, abrasion-resistant material, said cushioning material being laminated to and sandwiched between the adhesive layer and the layer of strong, abrasive-resistant material. The adhesive layer secures the orthopedic support to the footwear bottom surface and the abrasion-resistant material engages the support surface when the wear steps on the footwear and the orthopedic support supports the wearer's foot. Other features, advantages and objects of the present invention will become apparent with reference to the following detailed description and the accompanying drawings.

BRIEF DESCRIPTION OF DRAWINGS

FIG. 1 is a perspective view of the orthopedic support of the present invention;

FIG. 2A is a bottom view illustrating the position assumed by the orthopedic support when applied to footwear on a wearer's right foot;

FIG. 2B is a view similar to FIG. 2A but illustrating the position assumed by the orthopedic support when applied to the bottom of footwear on a wearer's left foot;

FIG. 3 is a side view of the orthopedic support;

FIG. 3A is an enlarged, partial sectional view taken along the line 3A—3A in FIG. 3; and FIG. 4 is a side view of the apparatus of the present invention.

PREFERRED MODE FOR CARRYING OUT THE INVENTION

Referring now to the drawings, an orthopedic support constructed in accordance with the teachings of the present invention is generally designated by reference numeral 10. The orthopedic support includes a layer of resilient, compressible cushioning material 12, preferably closed cell polyethylene foam.

Orthopedic support 10 further includes a layer of adhesive 14 and a layer 16 of strong, abrasive-resistant material such as natural or synthetic rubber. The cushioning material 12 is laminated to and sandwiched between the adhesive layer and layer 16. The adhesive may simply be coated onto the cushioning material and may be covered by a protective layer (not shown) prior to use. Any suitable means such as adhesive, heat bonding or the like may be utilized to secure layer 16 to the cushioning material.

The orthopedic support has a front end 20, a rear end 22, and opposed sides 24, 26 extending between the front and rear ends. Side 26 is, as may clearly be seen, longer than side 24 and the front end 20 of the orthopedic support is tapered and defines a protrusion 28.

In use, orthopedic support 10 is attached to footwear, such as shoe 30 (FIG. 4), having a heel portion 32, a toe portion 34, and an arch portion 36 between heel portion and toe portion. Footwear 30 has a bottom surface 38 defined by portions 32, 34, and 36.

The orthopedic support 10 is attached to footwear 30 by engaging the bottom surface 38 of the footwear with the adhesive layer 14. The orthopedic support is attached to the bottom surface at the arch portion 36. As may perhaps best be seen with reference to FIGS. 2A, 2B and 4, sides 24, 26 generally conform in shape to opposed sides of the arch portion, the orthopedic support being substantially confined to the area of the arch 5 portion whereby virtually all of the support for a wearer's foot is provided by the arch portion when the wearer steps on the footwear with the orthopedic support positioned on a support surface.

Orthopedic support 10 has a first thickness when in an unstressed condition, the cushioning material 12 compressing when the wearer steps on the footwear whereby the orthopedic support assumes a stressed condition having a second, lesser thickness.

The orthopedic support 10 when in either the stressed condition or the unstressed condition maintains the footwear 30 above and out of engagement with the support surface when the bottom of the wearer's foot is substantially parallel to the support surface as illustrated in FIG. 4.

It will be appreciated that when the wearer takes a step, the orthopedic support is completely removed from the ground or other support surface. When contact is re-established between the support surface and the orthopedic support, the support will first engage the support surface in the vicinity of rear end 22. As the wearer moves forward, his or her foot will tilt from a position where the heel is closer to the support surface than the toe, through an intermediate level position (shown in FIG. 4), to an end position whereat the toe of the foot is closer to the support surface than is the wearer's heel. The orthopedic support 10 non-uniformly compresses during this action.

At all times during engagement of the orthopedic support with the support surface the arch portion of the wearer's foot has an upwardly directed force applied thereto by the orthopedic support to support the wearer. It will be appreciated that as the foot tilts from the heel-down to the heel-up position the location of maximum force exerted upwardly by the orthopedic support will move generally forward from the vicinity of the rear end to the front end thereof. This exerts a massaging action through the footwear sole on the bottom of the wearer's foot which stimulates the circulation of blood therein. And, of course, the orthopedic support will ensure that the heel, ball and toe areas of the foot are significantly free of the impact normally caused by the act of walking.

As can be seen with reference to FIGS. 2A and 2B, the orthopedic support 10 is made available for application to either a left foot or a right foot. That is, there is a left foot model and a right foot model which is virtually a mirror-image thereof. The longer of the two opposed sides, i.e. side 26 is always positioned at the instep of the wearer's foot so that the foot will be supported at the arch portion over virtually all of the width thereof.

Rather than a shoe, the orthopedic support may be applied to footwear in the form of a sock. In such a case, it has been found advantageous to lengthen the distance between front end 20 and rear end 22 so that the orthopedic support will not only be more comfortable but exert its massaging action over a somewhat longer distance. Dash line 50 in FIG. 2A illustrates such an extension of length.

I claim:

1. In combination:

footwear having a heel portion, a toe portion and an arch portion between said heel portion and toe portion, said footwear having a bottom surface defined by said portions;

an orthopedic support having a flat bottom and a generally uniform thickness when in an unstressed condition, said orthopedic support including a layer of cushioning material attached to said footwear bottom surface at said arch portion, a layer of adhesive, and a layer of strong, abrasion-resistant material, said cushioning material being laminated to and sandwiched between said adhesive layer and said layer of strong, abrasive-resistant material, and said adhesive layer securing said orthopedic support to said footwear bottom surface, said orthopedic support having a front end, a rear end, and opposed sides extending between said front end, a rear end, and opposed sides extending between said front and rear ends and generally conforming in shape to opposed sides of said arch portion, said orthopedic support being substantially confined to the area of said arch portion whereby virtually all of the support for a wearer's foot is provided by said arch portion when said wearer steps on said footwear with said orthopedic support positioned on a support surface, said abrasion-resistant material engaging said support surface when the wearer steps on said footwear and said orthopedic support supports said wearer's foot and operable when either in said unstressed condition or in a stressed condition when said cushioning material is compressed when a wearer steps on said footwear to maintain said footwear above and out of engagement with said support surface when the bottom of the wearer's foot is substantially parallel to the support surface, said cushioning material being non-uniformly compressed along the length thereof when the bottom of the wearer's foot tilts relative to said support surface when said wearer takes a step, and said orthopedic support exerting an upwardly directed force against the wearer's foot having a maximum force location which moves generally forward from the vicinity of the rear end of the orthopedic support to the front end thereof as the foot tilts from heel-down to heel-up position to exert a massaging action on the bottom of the wearer's foot which stimulates the circulation of blood therein.

2. The combination according to claim 1 wherein said footwear is a conventional shoe having a sole defining said arch portion and said toe portion and a heel defining said heel portion and projecting downwardly from said sole, said orthopedic support being adhesively secured to said sole immediately adjacent to said heel and projecting downwardly beyond the plane occupied by the bottom of said heel both when said orthopedic support is in either said unstressed condition or said stressed condition.

3. The combination according to claim 1 wherein said cushioning material is closed cell plastic foam.

4. The combination according to claim 1 wherein said footwear is a sock.

5. The combination according to claim 1 wherein said opposed sides of said orthopedic support differ in length and wherein the front end of said orthopedic support is tapered and defines a protrusion, the longer of said opposed sides being positioned at the instep of the wearer's foot.

6. A method of promoting blood circulation in a wearer's foot while said foot is enclosed in footwear having an arch portion, comprising the steps of:
 applying an orthopedic support including a layer of cushioning material to said arch portion;
 confining said orthopedic support to said arch portion;
 walking on a support surface;
 during said walking, maintaining the heel and toe portions of said footwear substantially out of engagement with said support surface; and
 while said orthopedic support engages said support surface during walking, exerting a continuously variable massaging force on the arch portion of the wearer's foot.

* * * * *